United States Patent [19]
Fleming

[11] Patent Number: 5,711,313
[45] Date of Patent: Jan. 27, 1998

[54] DISCOVERABLE EARPLUG

[75] Inventor: Thomas Walter Fleming, San Diego, Calif.

[73] Assignee: Howard S. Leight & Associates, San Diego, Calif.

[21] Appl. No.: 785,415

[22] Filed: Jan. 23, 1997

[51] Int. Cl.$^6$ ............................................. A61F 11/00
[52] U.S. Cl. ............................ 128/864; 128/866; 2/209
[58] Field of Search .................................. 128/846, 864, 128/865, 866, 867; 2/68, 208, 209

[56] References Cited

U.S. PATENT DOCUMENTS

| | | | |
|---|---|---|---|
| 125,339 | 4/1872 | Sedgwick | 2/209 |
| 516,135 | 3/1894 | Thamm | 2/209 |
| 758,680 | 5/1904 | Otto | 2/209 |
| 955,276 | 4/1910 | Lopizich | 128/866 |
| 4,253,452 | 3/1981 | Powers | 128/864 |
| 4,936,411 | 6/1990 | Leonard | 128/864 |

Primary Examiner—Michael A. Brown
Attorney, Agent, or Firm—Freilich Hornbaker Rosen

[57] ABSTRACT

An earplug is described, with a metal insert that enables the earplug to be detected if it falls in a vat of food or other material during industrial processing, wherein the insert can be very easily attached, with or without a cord, to even an earplug body formed of resilient foam. The earplug includes a molded earplug body (12) having an axis (16) extending in forward and rearward directions. The earplug includes a detectable insert (14) attached to the rear portion (22) of the body, the insert comprising a fastener having a shaft (32) extending through a hole (30) in the rearward portion of the body and having a pair of flanges (34, 36) at opposite sides of the rearward portion, with foam body material compressed between the flanges. A cord (96) is attached to the earplug, the cord having a wrapped end part (110) that is wrapped around the shaft and which is compressed between a flange (34) and the compressed portion of the earplug body.

14 Claims, 2 Drawing Sheets

5,711,313

DISCOVERABLE EARPLUG

BACKGROUND OF THE INVENTION

Earplugs are worn by industrial workers to protect their hearing. However, when worn by workers in the food or pharmaceutical industry, there is danger of product contamination if an earplug should fall into the material being processed. Such industries use detectors for metallic and other objects, but such detectors usually cannot detect earplugs molded of foam plastic or other plastic or rubber. European patent publication 244,979 and U.S. Pat. 4,936,411 show a metal object inserted into a deep hole or channel extending along the axis of a solid rubber or other polymer earplug. It can require substantial cost to insert the object and securely lock it in place, especially if the earplug is formed of foam material. A metal object or other detectable insert, which could be very securely attached to earplugs, especially those of the compressible foam plastic type, and in a manner that enabled attachment at low cost, would be of value.

SUMMARY OF THE INVENTION

In accordance with one embodiment of the present invention, a detectable earplug is provided, which can be constructed at low cost. The earplug includes a molded earplug body having an axis extending in forward and rearward directions and having a forward portion that first enters a persons ear canal and having a rearward portion. The earplug also includes a detectable insert that is attached to the body. The insert comprises a fastener with a shaft extending through a lateral hole in the body between laterally opposite sides of the body. The fastener includes enlargements lying at laterally opposite sides of the body rearward portion. The body is preferably formed of a compressible resilient foam, with the body portion lying between the enlargements being compressed therebetween.

Where a cord is to be attached to the earplug and extend therefrom, an end portion of the cord can be trapped between the fastener and the earplug body. The cord can be wrapped about the shaft and trapped between a first of the enlargements and the body rearward portion that lies between the enlargements.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
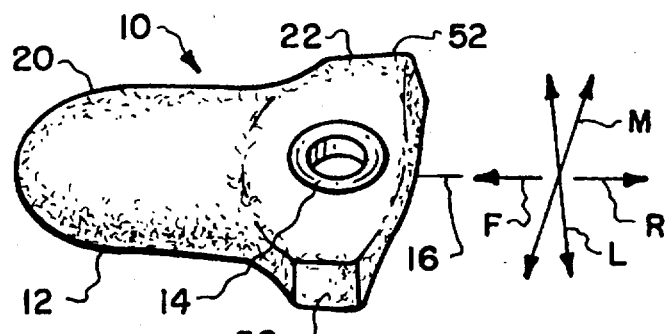
FIG. 1 is an isometric view of a detectable earplug of one embodiment of the present invention.
Figure 2:
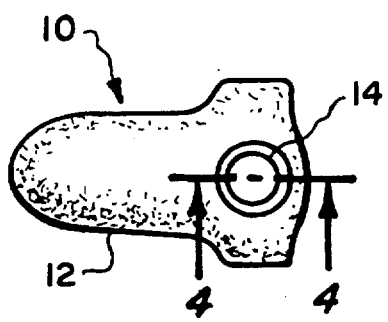
FIG. 2 is a side view of the earplug of FIG. 1, as taken along a lateral direction.

FIG. 1 illustrates a detectable earplug 10 which includes an earplug body 12 and a detectable insert 14 mounted on the body. The earplug body has an axis 16 extending in forward and rearward directions F, R. The body has a front portion 20 which is the portion that is initially inserted into a person's ear canal to block sound, and has a rearward portion 22, with the particular rearward portion shown being designed to lie outside the entrance to the ear canal. The earplug body 12 is generally of the shape shown in U.S. Pat. No. Des. 329,897. The body is molded of a soft polymer (modulus of elasticity of less than 50,000 psi), that is, a polymer that can be significantly compressed and/or deflected by forces of several ounces typically applied by the walls of the ear canal to an earplug, and has a much lower modulus of elasticity than engineering plastics (whose modulus of elasticity is more than 100,000 psi). The particular body 12 is formed of resilient plastic foam, such as slow recovery foam which is easily compressed and which takes about one minute to recover to near its original uncompressed shape.

Figure 4:
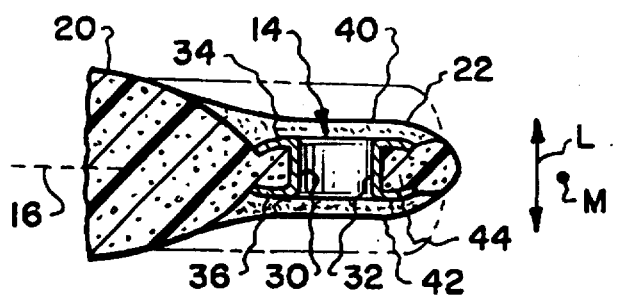
FIG. 4 is an enlarged sectional view taken on line 4—4 of FIG. 2.
Figure 3:
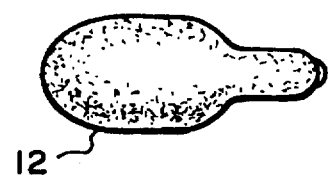
FIG. 3 is a side view of the earplug of FIG. 2, taken along a longitudinal direction.

As shown in FIG. 4, the earplug has a through hole 30 that extends in a lateral direction L which is perpendicular to the axis 16. The insert is in the form of a fastener such as an eyelet, which has a barrel or shaft 32 that projects through the hole 30 and which has flanges or enlargements 34, 36 at laterally opposite sides 40, 42 of the body rearward portion. The enlargements 34, 36 are shown as being in the form of washers that completely surround the shaft. A region 44 of the body that lies between the enlargements 34, 36, is highly compressed, by more than 20% of its original thickness, and usually by at least about 50% of its original thickness.

The insert 14 formed by a shaft that passes completely through the earplug rearward portion in a direction perpendicular to the axis of the earplug, enables simple and secure mounting of the insert. After the earplug body 12 is molded, in the same manner as for nondetectable earplugs, a through hole is formed in the earplug. Then the eyelet (14) is projected through the hole, the eyelet having a flange or enlargement at only one end. Thereafter, the other end of the eyelet is deformed to form the second enlargement 36, with the deformation proceeding until the region 44 of the body between enlargements is highly compressed. The eyelet is a very low cost item, and its installation can be achieved at low cost.

Applicant prefers to use an earplug body with longitudinally opposite sides 50, 52, which are longitudinally spaced in longitudinal direction M, by more than the width of the front portion 20 of the body. This provides side portions that can be easily grasped to withdraw the earplug. By contrast, the longitudinal middle of the body rear portion, has a lateral width (in direction L, FIG. 4) which is much less than the longitudinal width of the front portion 20 of the body. The result is to provide a thin but wide rear portion that can be readily grasped, to pull out the earplug.

Figure 5:
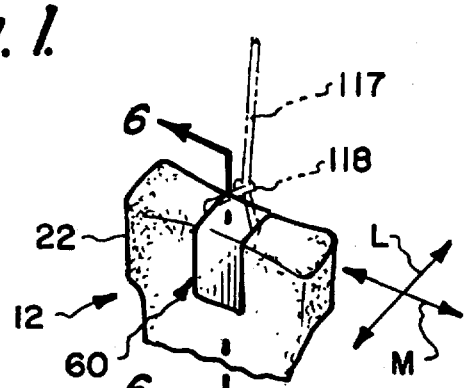
FIG. 5 is a partial isometric view of a detectable earplug constructed in accordance with another embodiment of the invention.
Figure 6:
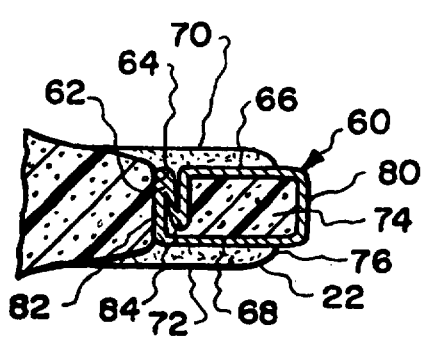
FIG. 6 is a view taken on line 6—6 of FIG. 5.
Figure 7:
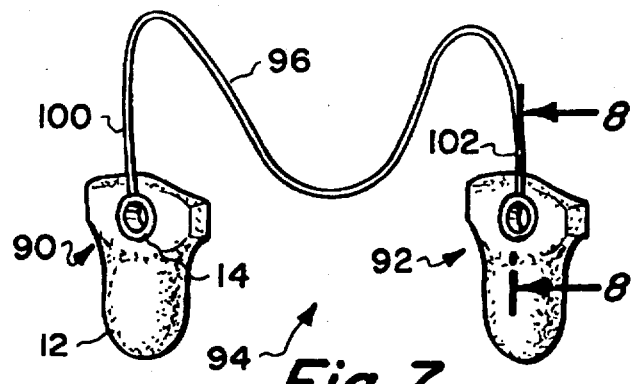
FIG. 7 is an isometric view of a detectable earplug assembly which includes two earplugs and a cord connecting them.

FIG. 5 illustrates the earplug body 12 with a different detectable insert 60 attached to the rear portion 22 of the body. As shown in FIG. 6, the insert 60 forms a fastener with a shaft 62 extending in a lateral direction L completely through a hole 64 in the body. The fastener formed by the insert includes enlargements 66, 68 lying on lateral opposite sides 70, 72 of the body rearward portion, and with the body including a region 74 that is tightly squeezed between the enlargements. The enlargements 66, 68 of the particular insert shown, extend to the rear edge 76 of the body, where they are joined by an insert rear end 80. The shaft 62 includes two shaft parts 82, 84 which lock together when the insert is installed on the body.

FIGS. 7-10 illustrate a pair of detectable earplugs 90, 92 of an earplug assembly 94 that includes a cord 96 having opposite end portions or ends 100, 102 that are securely fixed to the earplugs. The presence of a cord that joins the earplugs, makes it less likely that one of the two earplugs will be dropped. Each of the earplugs such as 90, includes an earplug body 12 and a detectable insert 14 which is securely fastened to the body. Applicant uses the insert 14 to securely hold a corresponding end 100 of the cord.

Figure 8:
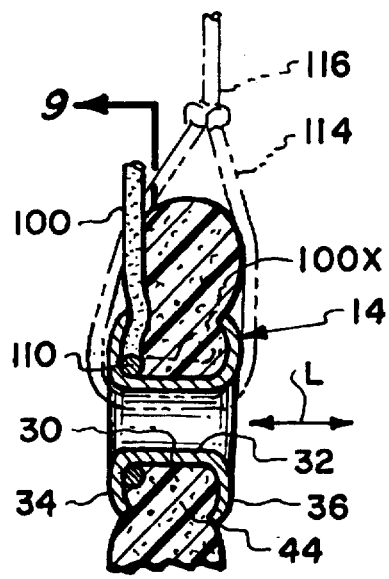
FIG. 8 is a view taken on line 8—8 of FIG. 7.
Figure 9:
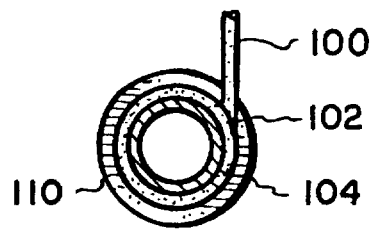
FIG. 9 is a sectional view taken on line 9—9 of FIG. 8, showing only the fastener and cord.
Figure 10:
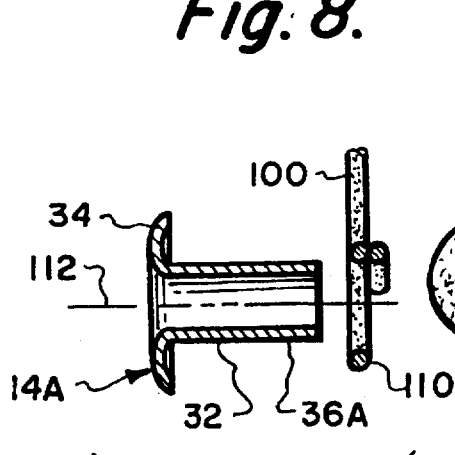
FIG. 10 is an exploded view showing one manner in which the fastener and cord of FIG. 8 can be assembled.

As shown in FIGS. 8 and 9, the cord end 100 is wrapped about the shaft 32 of the insert and is trapped between a compressed region 44 of the earplug body and an enlargement 34 of the insert that presses against the compressed body portion. Applicant prefers that the cord end 100 be wrapped more than 360° about the shaft, and with the cord having overlapping areas 102, 104 that are fastened together, as with adhesive. FIG. 10 shows one example of the manner in which the cord end 100 can be installed on the insert. The insert is shown in its initial configuration 14A, wherein one of the enlargements at 36A has not yet been radially outwardly deformed. The cord is formed into the loop 110, and the loop is slid over the insert shaft 32 and against the already formed enlargement 34. A hole is formed in the rearward portion of the earplug body, and the insert 14A with the cord loop 110 installed thereon, is pressed through the hole. Then, the initial enlargement area at 36A is deformed radially outwardly (with respect to the shaft axis 112) until the enlargement assumes the shape shown at 36 in FIG. 8. The enlargement 34 can be formed with its radially outer edge bent to assure that the cord is not weakened.

The cord end 100 can be securely coupled to the insert 14 in a number of ways, including wrapping the cord so it extends axially, or in the lateral direction L, between the opposite enlargements, as indicated at 100X. Another way is to thread the cord through a hole in the shaft 32 and to tie a knot or other enlargement at the extreme end of the cord.

FIG. 8 shows, in phantom lines, a cord at 114 that extends in a loop through the hollow shaft of the eyelet insert 14, with the cord tied to itself at 116. FIG. 5 shows, in phantom lines, a cord at 117 that extends in a loop through the insert 60 and with the cord held to itself at 118.

The hole 30 in the body can be formed by thrusting a sharp-pointed piercing tool through the body or by punching out a piece of material of the body. Applicant prefers to merely pierce the body, with a piercing tool whose cross section is in the shape of a cross.

Figure 11:
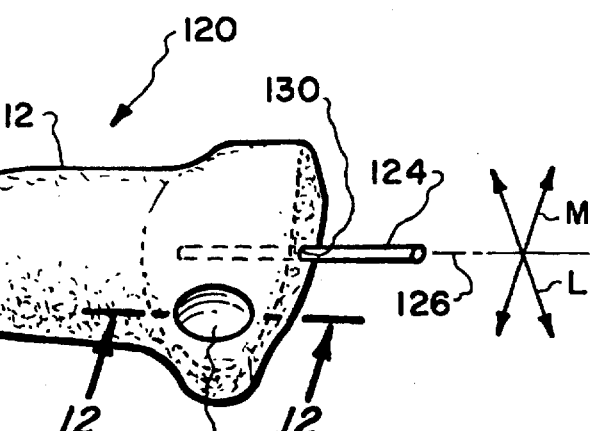
FIG. 11 is an isometric view of a detectable earplug of another embodiment of the invention.
Figure 12:
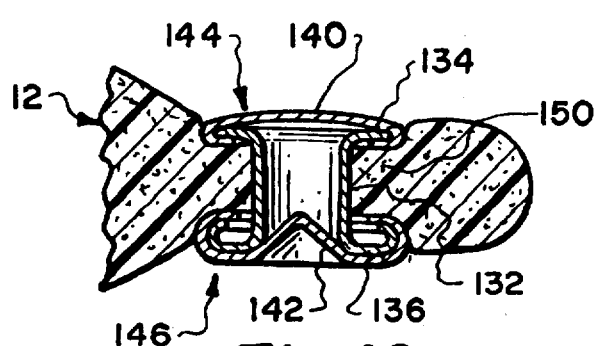
FIG. 12 is a sectional view taken on line 12—12 of FIG. 11.

FIGS. 11 and 12 illustrate another earplug 120 that includes an earplug body 12 of the same construction as in FIG. 1, and a detectable insert 122 and cord end 124. The insert is a rivet that is offset from the earplug body axis 126, and that extends primarily perpendicular to the axis through the body. The cord end 124 lies in a hole 130 that extends along the axis of the body, and is glued in place. This construction can be useful where tooling is already setup to install the cord as shown, and it is desired to add the detectable insert 122 for special applications.

Figure 12A:
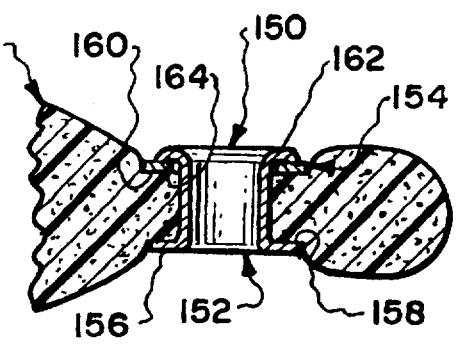
FIG. 12A is a sectional view similar to FIG. 12, but with another insert.

FIG. 12 shows that the insert includes a shaft 132 with opposite flanges 134, 136. Caps 140, 142 are fastened around the flanges to give a more "finished" look. The caps also add metal for easier detection, and avoid edges on the enlargements 144, 146 formed by the flanges and caps, that can cut into the compressed region 150 of the body and allow the insert to pullout. FIG. 12A shows a lower cost alternative, where the insert 150 includes an eyelet 152 and a washer 154. The eyelet is supplied with an enlargement 156 having a flat face 158 that presses against the earplug body 12. The washer 154 has a flat face 160, and is held down by a rolled-over eyelet flange 162 that has a concave lower face 164.

Applicant prefers to use an insert merely formed of metal (or other conductive material) for detection by reason of its conductivity, or of a magnetic material such as steel which can be detected by its magnetic properties. However, it is also possible to form the insert with a tiny circuit that is resonant to a predetermined frequency and which, when energized, emits high frequency energy that can be detected.

Thus, the invention provides a detectable earplug which includes a molded earplug body and a detectable insert that is attached to the rear body, where the insert comprises a fastener with a shaft that projects through a hole extending primarily perpendicular to the axis of the earplug and having enlargements extending from the shaft and lying at opposite sides of the body. The lateral direction could be the direction M of FIG. 1, wherein a longer insert would be used. Where the body is formed of resilient foam material, the enlargements can compress a region of the body lying between them, to provide a secure and low cost fastening of the insert to the resilient foam body. Where it is desired to attach an end portion of a cord to the earplug, this can be readily accomplished by coupling the cord to the insert.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A noise-blocking detectable earplug comprising:
   an earplug body having an axis extending in forward and rearward directions, said earplug having a forward portion constructed to fit into a human ear canal and block noise thereat;
   remotely detectable insert that includes electrically conductive material attached to said body;
   said insert comprising a fastener with a shaft extending primarily in a lateral direction, which is perpendicular to said axis, through said body.

2. The detectable earplug described in claim 1 wherein:
   said body has laterally opposite sides, with said fastener having enlargements lying at said laterally opposite sides of said body.

3. The detectable earplug described in claim 2 wherein:
   said body is formed of an elastic polymer and said body is compressed between said enlargements.

4. The detectable earplug described in claim 1 including:
   a cord having an end portion connected to said fastener, said cord end portion includes a part that is wrapped about said shaft and is trapped between a first of said enlargements and said body rearward portion.

5. The detectable earplug described in claim 1 including:

a cord having an end portion connected to said fastener, said shaft is hollow and said cord extends in a loop through said hollow shaft.

6. The detectable earplug described in claim 1 where in:

said body is formed of a compressible resilient foam polymer and has laterally opposite sides, and said fastener has enlargements at said laterally opposite sides of said body, said enlargements lying opposite each other with a region of said body lying between said enlargements, and with said region of said body being compressed by more than 20% of its original thickness between said enlargements.

7. The detectable earplug described in claim 1 wherein:

said body is formed of an elastic polymer and said insert fastener is formed of metal, said shaft has opposite ends and said fastener has flanges that extend from opposite ends of said shaft and that compress said body.

8. A detectable earplug comprising:

an earplug body having an axis extending in forward and rearward directions, said body having a forward portion constructed to fit in the ear canal of a person and block the passage of sound therein, and said body having a rearward portion;

a detectable insert attached to said rearward portion of said body;

said body being formed of molded resiliently compressible foam material with said rear portion having a through hole therein which extends primarily in a perpendicular direction that is perpendicular to said axis, with said rearward portion having opposite sides spaced in said perpendicular direction;

said insert having a portion that projects through said hole and a pair of flanges lying against said opposite sides of said body rear portion beside said hole;

said body rearward portion being tightly squeezed between said flanges.

9. The detectable earplug described in claim 8 wherein:

said insert is in the form of an eyelet comprising a shaft with a central hole forming said portion that projects through said hole, said eyelet including said flanges at opposite ends of said shaft.

10. The detectable earplug described in claim 8 including:

a cord having an end connected to said insert.

11. A method for constructing an earplug so it can be readily detected if it falls into a quantity of nonmetallic material, comprising:

forming an earplug body of polymer material so it has an axis extending in front and rear directions, and so it has a front portion shaped to fit into the ear canal of a person and so it has a rear portion;

installing a detectable electrically conductive fastener on said body rear portion, including projecting a fastener shank that has opposite ends, in primarily a lateral direction that is perpendicular to said axis, completely through said body rear portion, and establishing flanges that project from said opposite ends of said shank against surface areas of said body rear portion that lie immediately around said shank to lock said shank in place.

12. The method described in claim 11 wherein:

said steps of forming an earplug body includes molding it of resilient foam material, and said step of establishing flanges includes compressing said foam material between said flanges.

13. A detectable earplug comprising:

an earplug body having an axis extending in forward and rearward directions;

a detectable insert attached to said body, said insert comprising an eyelet having a shaft extending primarily in a lateral direction, which is perpendicular to said axis, through said body;

said eyelet having a rolled-over flange and having a washer lying between said rolled-over flange and a region of said body, said rolled-over flange having a concave surface lying against said washer and said washer having a flat face lying against said region of said body.

14. A method for constructing an earplug so it can be readily detected if it falls into a quantity of nonmetallic material, comprising:

forming an earplug body of polymer material so it has an axis extending in front and rear directions, and so it has a front portion shaped to fit into the ear canal of a person and so it has a rear portion;

installing a detectable fastener on said body rear portion, including projecting a fastener shank that has opposite ends, in primarily a lateral direction that is perpendicular to said axis, completely through said body rear portion, and establishing flanges that project from said opposite ends of said shank against surface areas of said body rear portion that lie immediately around said shank to lock said shank in place;

said step of establishing flanges includes placing a washer around an end of said shank, and deforming said shank into a flange that presses said washer against said body rear portion.

* * * * *